US009227980B2

(12) United States Patent
Scherman et al.

(10) Patent No.: US 9,227,980 B2
(45) Date of Patent: Jan. 5, 2016

(54) METHODS FOR THE PURIFICATION OF CUCURBITURIL (75) Inventors: Oren Alexander Scherman, Cambridge (GB); Dezhi Jiao, Cambridge (GB); Nan Zhao, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 652 days.

(21) Appl. No.: 13/518,661

(22) PCT Filed: Dec. 23, 2010

(86) PCT No.: PCT/GB2010/002330
§ 371 (c)(1),
(2), (4) Date: Jun. 22, 2012

(87) PCT Pub. No.: WO2011/077099
PCT Pub. Date: Jun. 30, 2011

(65) Prior Publication Data
US 2013/0012721 A1 Jan. 10, 2013

(30) Foreign Application Priority Data
Dec. 23, 2009 (GB) .................................. 0922623.4

(51) Int. Cl.
C07D 487/22 (2006.01)

(52) U.S. Cl.
CPC .................................. C07D 487/22 (2013.01)

(58) Field of Classification Search
None
See application file for complete search history.

(56) References Cited

U.S. PATENT DOCUMENTS

| 2002/0133003 A1 | 9/2002 | Kim et al. |
| 2006/0154254 A1 | 7/2006 | Kim et al. |
| 2006/0292570 A1 | 12/2006 | Keinan |

FOREIGN PATENT DOCUMENTS

| JP | A-2007-211060 | 8/2007 |
| WO | WO 2005/023816 A2 | 3/2005 |
| WO | WO 2007/014214 A2 | 2/2007 |
| WO | WO 2007/046575 A1 | 4/2007 |
| WO | WO 2007/106144 A1 | 9/2007 |
| WO | WO 2008/096360 A2 | 8/2008 |
| WO | WO 2009/071899 A2 | 6/2009 |

OTHER PUBLICATIONS

Jiao, D. et al., "Isolation of cucurbit[n]uril homologues with imidazolium salts in a recyclable manner," Green Chemistry, 2012, pp. 2445-2449, vol. 14.
Mukhopadhyay, P. et al., "Social Self-Sorting in Aqueous Solution," Journal of Organic Chemistry, 2004, pp. 6157-6164, vol. 69, No. 19.
Busetti, A. et al., "Antimicrobial and antibiofilm activities of 1-alkylquinolinium bromide ionic liquids," Green Chemistry, 2010, pp. 420-425, vol. 12.
Day, A. I. et al., "The Effects of Alkali Metal Cations on Product Distributions in Cucurbit[n]uril Synthesis," Journal of Inclusion Phenomena and Macrocyclic Chemistry, 2002, pp. 247-250, vol. 43.
European Office Action issued in European Patent Application No. 10 800 981.2 on Jun. 27, 2013.
Chinese Office Action issued in Chinese Patent Application No. 201080064589.1 on Dec. 17, 2013.
Bosman et al.; "Supramolecular polymers at work;" Materials Today; Apr. 2004; pp. 34-39; vol. 7; Elsevier Ltd.
Sijbesma et al.; "Reversible Polymers Formed from Self-Complementary Monomers Using Quadruple Hydrogen Bonding;" Science; 1997; pp. 1601-1604; vol. 278; American Association for the Advancement of Science; Washington D.C.
Archer et al.; "Coordination chemistry from monomers to copolymers;" Coordination Chemistry Reviews; 1993; pp. 49-68; vol. 128; Elsevier Sequoia.
Swiegers et al.; "New Self-Assembled Structural Motifs in Coordination Chemistry;" Chem. Rev.; 2000; pp. 3483-3537; vol. 100; American Chemical Society.
Lehn et al.; "Spontaneous assembly of double-stranded helicates from oligobipyridine ligands and copper(I) cations: Structure of an inorganic double helix;" Proc. Natl. Acad. Sci.; May 1987; pp. 2565-2569; vol. 84.
Schütte et al.; "Metallosupramolecular Thin Polyelectrolyte Films;" Angew. Chem. Int. Ed.; 1998; pp. 2891-2893; vol. 37, No. 20; Wiley-VCH Verlag GmbH & Co.
Lohmeijer et al.; "Supramolecular Engineering with Macromolecules: An Alternative Concept for Block Copolymers;" Angew. Chem. Int. Edu.; 2002; pp. 3825-3829; vol. 41, No. 20; Wiley-VCH Verlag GmbH & Co.
Chen et al; "Ruthenuim Bipyridine-Containing Polymers and Block Copolymers via Ring-Opening Metathesis Polymerization;" Macromolecules; 2004; pp. 5866-5872; vol. 37; American Chemical Society.
Zhou et al.; "Synthesis and Characterization of Bis(2,2':6',2"-terpyridine)ruthenium(II)-Connected Diblock Polymers via RAFT Polymerization;" Macromolecules; 2005; pp. 4114-4123; vol. 38; American Chemical Society.
Fustin et al.; "Metallo-Supramolecular Block Copolymers;" Advanced Materials; 2007; pp. 1665-1673; vol. 19; Wiley-VCH Verlag GmbH & Co.
Scherman et al.; "Olefin metathesis and quadruple hydrogen bonding: A powerful combination in multistep supramolecular synthesis;" PNAS; Aug. 8, 2006; pp. 11850-11855; vol. 103, No. 32; The National Academy of Sciences of the USA.
Yang et al.; "Supramolecular AB Diblock Copolymers;" Angew. Chem. Int. Ed.; 2004; pp. 6471-6474; vol. 43; Wiley-VCH Verlag GmbH & Co.

(Continued)

Primary Examiner — Noble Jarrell
(74) Attorney, Agent, or Firm — Oliff PLC (57) ABSTRACT

A method for purifying a cucurbituril from a mixture. The method includes the step of forming a complex between the cucurbituril and a cucurbituril guest. The complex has altered physical and/or chemical properties to the cucurbituril which allow the complex to be separated from at least one other component of the mixture. The mixture includes the cucurbituril, the other component and a solvent.

13 Claims, 2 Drawing Sheets (56) References Cited

OTHER PUBLICATIONS

Higley et al.; "A Modular Approach toward Block Copolymers;" Chem. Eur. J.; 2005; pp. 2946-2953; vol. 11; Wiley-VCH Verlag GmbH & Co.
Yamauchi et al.; "Combinations of Microphase Separation and Terminal Multiple Hydrogen Bonding in Novel Macromolecules;" J. Am. Chem. Soc.; 2002; pp. 8599-8604; vol. 124; American Chemical Society.
Binder et al.; "Supramolecular Poly(ether ketone)-Polyisobutylene Pseudo-Block Copolymers;" Journal of Polymer Science: Part A: Polymer Chemistry; 2004; pp. 162-172; vol. 42; Wiley Periodicals, Inc.
Söntjens et al.; Stability and Lifetime of Quadruply Hydrogen Bonded 2-Ureido-4[1H]-pyrimidinone Dimers; J. Am. Chem. Soc.; 2000; pp. 7487-7493; vol. 122; American Chemical Society.
Shimizu; "Mini Review-Perspectives on main-chain hydrogen bonded supramolecular polymers;" Polymer International; 2007; pp. 444-452; vol. 56; Society of Chemical Industry.
Behrend et al.; "Justus Liebig's Annalen Der Chemie.;" 1904; pp. 1-37; vol. 339.
Freeman et al.; "Cucurbituril;" J. Am. Chem. Soc.; 1981; pp. 7367-7368; vol. 103; American Chemical Society.
Kim et al.; "New Cucurbituril Homologues: Syntheses, Isolation, Characterization, and X-ray Crystal Structures of Cucurbit[n]uril (n=5, 7, and 8);" J. Am. Chem. Soc.; 2000; pp. 540-541; vol. 122; American Chemical Society.
Lagona et al.; "The Cucurbit[n]uril Family;" Angew. Chem. Int. Ed.; 2005; pp. 4844-4870; vol. 44; Wiley-VCH Verlag GmbH & Co.
Kim et al.; "Selective Inclusion of a Hetero-Guest Pair in a Molecular Host: Formation of Stable Charge-Transfer Complexes in Cucurbit[8]uril;" Angew. Chem. Int. Ed.; 2001; pp. 1526-1529; vol. 40, No. 8; Wiley-VCH Verlag GmbH.
Sindelar et al.; "Supramolecular Assembly of 2,7-Dimethyldiazapyrenium and Cucurbit[8]uril: A New Fluorescent Host for Detection of Catechol and Dopamine;" Chem. Eur. J.; 2005; pp. 7054-7059; vol. 11; Wiley-VCH Verlag GmbH & Co.
Bush et al.; "Charge-Mediated Recognition of N-Terminal Tryptophan in Aqueous Solution by a Synthetic Host;" J. Am. Chem. Soc.; 2005; pp. 14511-14517; vol. 127; American Chemical Society.
Jeon et al.; "Supramolecular Amphiphiles: Spontaneous Formation of Vesicles Triggered by Formation of a Charge-Transfer Complex in a Host;" Angew. Chem. Int. Ed.; 2002; pp. 4474-4476; vol. 41, No. 23; Wiley-VCH Verlag GmbH & Co.
Jeon et al.; "Molecular Loop Lock: A Redox-Driven Molecular Machine Based on a Host-Stabilized Charge-Transfer Complex;" Angew. Chem. Int. Ed.; 2005; pp. 87-91; vol. 44; Wiley-VCH Verlag GmbH & Co.
Ko et al.; "Designed Self-Assembly of Molecular Necklaces Using Host-Stabilized Charge-Transfer Interactions;" J. Am. Chem. Soc.; 2004; pp. 1932-1933; vol. 126; American Chemical Society.
Kim et al.; "Growth of poly(pseudorotaxane) on gold using host-stabilized charge-transfer interaction;" Chem. Commun.; pp. 848-849; The Royal Society of Chemistry, 2004.
Jeon et al.; "A [2]Pseudorotaxane-Based Molecular Machine: Reversible Formation of a Molecular Loop Driven by Electrochemical and Photochemical Stimuli;" Angew. Chem. Int. Ed.; 2003; pp. 4097-4100; vol. 42; Wiley-VCH Verlag GmbH & Co.
Ko et al.; "Supramolecular assemblies built with host-stabilized charge-transfer interactions;" Chem. Commun.; pp. 1305-1315; The Royal Society of Chemistry, 2007.
Moon et al.; "Cucurbit[8]uril-Mediated Redox-Controlled Self-Assembly of Viologen-Containing Dendrimers;" Angew. Chem. Int. Ed.; 2004; pp. 5496-5499; vol. 43; Wiley-VCH Verlag GmbH & Co.
Wang et al.; "Electrochemical Switching and Size Selection in Cucurbit[8]uril-Mediated Dendrimer Self-Assembly;" Angew. Chem. Int. Ed.; 2006; pp. 7042-7046; vol. 45; Wiley-VCH Verlag GmbH & Co.

Floudas et al.; "Poly(ethylene oxide-b-isoprene) Diblock Copolymer Phase Diagram;" Macromolecules; 2001; pp. 2947-2957; vol. 34; American Chemical Society.
Hwang et al.; "Noncovalent Immobilization of Proteins on a Solid Surface by Cucurbit[7]uril-Ferrocenemethylammonium Pair, a Potential Replacement of Biotin-Avidin Pair;" J. Am. Chem. Soc.; 2007; pp. 4170-4171; vol. 129; American Chemical Society.
Sun et al.; "The photoinduced long-lived charge-separated state of Ru(bpy)$_3$-methylviologen with cucurbit[8]uril in aqueous solution;" Chem. Commun; 2006; pp. 4195-4197; The Royal Society of Chemistry, 2006.
Jon et al.; "A facile, stereoselective [2+2] photoreaction mediated by cucurbit[8]uril;" Chem. Commun.; 2001; pp. 1938-1939; The Royal Society of Chemistry, 2001.
Rauwald et al.; "Supramolecular Block Copolymers with Cucurbit[8]uril in Water;" Angew. Chem. Int. Ed.; 2008; pp. 3950-3953; vol. 47; Wiley-VCH Verlag GmbH & Co.
Broeren et al.; "Multivalency in the Gas Phase: The Study of Dendritic Aggregates by Mass Spectrometry;" Angew. Chem. Int. Ed.; 2004; pp. 3557-3562; vol. 43; Wiley-VCH Verlag GmbH & Co.
Osaka et al.; "Characterization of host-guest complexes of cucurbit[n]uril (n=6,7) by electrospray ionization mass spectrometry;" J. Mass Spectrom; 2006; pp. 202-207; vol. 41; John Wiley & Sons, Ltd.
Brunsveld et al.; "Supramolecular Polymers;" Chem. Rev.; 2001; pp. 4071-4097; vol. 101; American Chemical Society.
Knapp et al.; "A Novel Synthetic Strategy toward Soluble, Well-Defined Ruthenium(II) Coordination Polymers;" Macromolecules; 1996; pp. 478-480; vol. 29; American Chemical Society.
Kim et al.; "Direct Synthesis of Polymer Nanocapsules with a Noncovalently Tailorable Surface;" Angew. Chem. Int. Ed.; 2007; vol. 46, pp. 3471-3474; Wiley-VCH Verlag GmbH & Co.
Ligthart et al.; "Supramolecular Polymer Engineering;" Macromolecular Engineering, Precise Synthesis, Materials Properties, Applications; 2007; pp. 351-399; Wiley-VCH Verlag GmbH & Co.
Lee et al., "Cucurbituril Homologues and Derivatives: New Opportunities in Supramolecular Chemistry", Acc. Chem. Res. 2003, 36, pp. 621-630.
Hennig et al., "Label-free continuous enzyme assays with macrocycle-fluorescent dye complexes", Nature Methods, vol. 4, No. 8, pp. 629-632, Aug. 2007.
Gadde et al., "Control of H- and J-Aggregate Formation via Host-Guest Complexation using Cucurbituril Hosts", J.Am.Chem.Soc. 2008, 130, pp. 17114-17119.
Zeng et al., "Enhancement of Energy Utilization in Light-Harvesting Dendrimers by the Pseudorotaxane Formation at Periphery", J.Am. Chem.Soc. 2009, 131, pp. 9100-9106.
Day et al., "Controlling Factors in the Synthesis of Cucurbituril and Its Homologues", J. Org. Chem. 2001, 66, pp. 8094-8100.
Marquez et al., "Cucurbiturils: Molecular Nanocapsules for Time-Resolved Fluorescence-Based Assays", IEEE Transactions on Nanobioscience, vol. 3, No. 1, Mar. 2004, pp. 39-45.
Huang et al., "Cucurbit[n]uril Formation Proceeds by Step-Growth Cyclo-oligomerization", J. Am. Chem. Soc. 2008, 130, pp. 8446-8454.
Dzyuba et al., "Influence of Structural Variations in 1-Alkyl(aralkyl)-3-Methylimidazolium Hexafluorophosphates and Bis(trifluoromethyl-sulfonyl)imides on Physical Properties of the Ionic Liquids", CHEMPHYSCHEM 2002, 3, pp. 161-166, Wiley-VCH-Verlag GmbH, 69451 Weinheim, Germany.
Liu et al., "Ionic liquids as novel guests for cucurbit[6]uril in neutral water", Chem. Comm., 2008, pp. 1070-1072.
Montes-Navajas et al., "Supraniolecular ionic liquids based on host-guest cucurbituril imidazolium complexes", ScienceDirect, Journal of Molecular Catalysis A: Chemical 279 (2008) pp. 165-169.
Miskolczy et al., "Inclusion Complex Formation of Ionic Liquids and Other Cationic Organic Compounds with Cucurbit[7]uril Studied by 4',6-Diamidino-2-phenylindole Fluorescent Probe", J. Phys. Chem. B 2009, 113, pp. 1645-1651.
Kolman et al., "Electron Density Shift in Imidazolium Derivatives upon Complexation with Cucurbit[6]uril", Chem. Eur. J. 2009, 15, pp. 6926-6931, Wiley-VCH Verlag GmbH & Co. KGaA, Weinheim.

(56) References Cited

OTHER PUBLICATIONS

Bonneau et al., "Rapid solid-state synthesis of materials from molybdenum disulphide to refractories", Nature, vol. 349, Feb. 7, 1991.

Gibson et al., "Solid State Metathesis Reactions in Various Applications", *Z. Anorg. Allg. Chem.* 2003, 629, pp. 1863-1870, Wiley-VCH Verlag GmbH & Co. KGaA, 69451 Weinheim.

He et al., "Synthesis and characterization of submicron-sized $LiNi_{1/3}Co_{1/3}Mn_{1/3}O_2$ by a simple self-propagating solid-state metathesis method", Science Direct, Journal of Power Sources 163 (2007) pp. 1053-1058.

Jiao et al., "A Systems Approach to Controlling Supramolecular Architecture and Emergent Solution Properties via Host-Guest Complexation in Water", J. Am. Chem. Soc. 2010, 132, pp. 15734-15743.

Liu et al., "Controlled catch and release of small molecules with cucurbit[6]uril via a kinetic trap", Chem. Commun., vol. 45, No. 22, 2009, pp. 3243-3245.

Jiao et al., "A "green" method for isolation of cucurbit[7]uril via a solid state metathesis reaction", Chem. Commun., 2010, vol. 46, No. 12, pp. 2007-2009.

Nov. 3, 2009 International Search Report issued in corresponding International Application No. PCT/GB2008/004016.

Nov. 3, 2009 Written Opinion of the International Searching Authority issued in corresponding International Application No. PCT/GB2008/004016.

May 12, 2010 Search Report issued in Great Britain Application No. 0922623.4.

Jul. 22, 2011 International Search Report issued in International Application No. PCT/GB2010/002330.

Jul. 28, 2014 Notice of Allowance issued in European Application No. 10800981.2.

Aug. 22, 2014 Office Action in Chinese Application No. 201080064589.1.

Apr. 10, 2015 Office Action issued in Chinese Application No. 201080064589.1.

METHODS FOR THE PURIFICATION OF CUCURBITURIL

PRIORITY

This application claims priority to GB 0922623.4, filed on 23 Dec. 2009, the contents of which are hereby incorporated by reference in their entirety.

FIELD OF THE INVENTION

This invention relates to methods for the purification of a cucurbituril from a mixture, preferably a mixture further comprising other cucurbituril forms.

BACKGROUND

The cucurbit[n]uril (CB[n]) family has been extensively studied in recent years on account of their scope within the fields of molecular recognition and aqueous self-assembly. [1] CB[7], a member of the CB[n] family, has a substantially higher water solubility than CB[6] and CB[8] and a larger binding cavity than its water soluble brother, CB[5].[2]

Recent reports have shown that CB[7] is an excellent host for binding and stabilising a wide range of small molecules, such as fluorescent dyes,[3] controlling aggregate formation of guest molecules,[4] and for use in light-harvesting systems.[5] However, a major drawback which has limited the study and application of CB[7] is its difficult isolation and purification from the synthesised mixture of CB[n] homologues.

Traditional isolation methods of CB[7] are based on the different solubilities of CB[n] in various solvents, such as acetone/water and methanol/water mixtures, limiting the overall yield of CB[7] to just under 3%.[6, 7] Nau et al. [8] has reported a more direct approach to preparing CB[7] by controlling the direct reaction of formaldehyde, glycoluril and sulfuric acid, followed by a similar isolation methodology based on solubility of CB[7] in an acetone/water mixture. This method gives a substantially better yield with higher purity, however, the separation and purification is still based primarily on solubility differences in a variety of mixed solvents. For the standard separation routes, it is difficult to obtain CB[7] in high purity as both CB[5] and CB[7] have low solubility in the mixed solvent systems (either acetone/$H_2O$ or $MeOH/H_2O$), requiring multiple solvent-based separation cycles.

Another isolation method which has been reported by Isaacs et al. uses column chromatography with a harsh acidic eluent $HCO_2H$ (88%):HCl (0.2 M) (1:1 v/v).[9] This can be a highly toxic process which results in acidic products and may limit the viability of scale-up.

The use of alkyl imidazolium salts to form complexes with cucurbituril compounds has been described [18], although this disclosure was made after the priority date of the present application.

Herein is reported a new cucurbituril isolation method which is convenient for obtaining pure cucurbituril material, is inherently more environmentally friendly and suitable for large scale purification by exploiting the reversible association and dissociation of a host-guest complex in a controlled manner.

SUMMARY OF THE INVENTION

The present invention provides a method for purifying a cucurbituril from a mixture. The method comprises the step of forming a complex between the cucurbituril and a cucurbituril guest. The complex has altered physical and/or chemical properties to the cucurbituril which allow the complex to be separated from at least one other component of the mixture.

Thus, in a first aspect of the invention there is provided a method for the purifying a cucurbituril from a mixture, the method comprising the steps of:
  providing a mixture comprising the cucurbituril and at least one other component;
  introducing to the mixture a cucurbituril guest, thereby to form a guest-host complex between the guest and the cucurbituril;
  separating the guest-host complex from at least one component of the mixture thereby to purify the cucurbituril from the other component.

The mixture comprises at least a cucurbituril, at least one other component and a solvent. One or more cucurbituril guests may be added to the mixture thereby to form a guest-host complex between the guest or guests and the cucurbituril. Thus, the method comprises the steps of:
  providing a mixture comprising the cucurbituril and at least one other component in a solvent;
  introducing to the mixture a cucurbituril guest or guests, thereby to form a guest-host complex between the guest or guests and the cucurbituril;
  separating the guest-host complex from at least one component of the mixture, and optionally the solvent also, thereby to purify the cucurbituril from the other component.

The mixture is preferably an aqueous mixture.

The cucurbituril is preferably CB[7]. The other component is preferably CB[5]. In an alternative embodiment, the cucurbituril is CB[8] and the other component is CB[6], or the cucurbituril is CB[6] and the other component is CB[8].

The cucurbituril guest is preferably an ionic liquid, and most preferably a compound, including a salt, comprising an imidazolium moiety.

The present invention also provides a cucurbituril obtained by the method of the invention.

Also provided by the present invention is a mixture comprising a complex of a cucurbituril with an ionic liquid, and further comprising another cucurbituril.

DETAILED DESCRIPTION OF THE INVENTION

The present inventors have identified a method whereby a guest molecule may be used to generate a guest-host complex with a cucurbituril. The guest-host complex may have altered physical and/or chemical properties compared to the uncomplexed cucurbituril. This change in physical and/or chemical properties may be used to purify the cucurbituril, as a guest-host complex, from a mixture that also comprises another component. After purification, the guest-host complex may optionally be decomplexed to obtain the cucurbituril.

The mixture comprises the cucurbituril, the other component and a solvent, preferably water. Thus, the method of the invention particularly relates to the separation of a cucurbituril from a non-solvent component. Nevertheless, the methods described herein may also be used to separate the cucurbituril from the other component and the solvent.

The methods of the invention encompass the use of two guest molecules to form a guest-host complex between the guests and the cucurbituril. A reference in the text to a cucurbituril guest may therefore be taken to be a reference to two guests also, which are capable of forming a complex with a cucurbituril. The guests may be the same or they may be different.

In a preferred embodiment, the solubility of the guest-host complex is different to that of the cucurbituril.

The mixture may be an aqueous mixture.

In one embodiment, the mixture comprises another cucurbituril structure, and the method relates to the separation of these structures.

A cucurbituril guest is used to generate a guest-host complex with the cucurbituril. The cucurbituril guest is selective for the cucurbituril over the other component in the mixture. For example, the cucurbituril guest is selective for the cucurbituril over another cucurbituril present in the mixture.

Cucurbituril

In one embodiment, the cucurbituril is a CB[6], CB[7], CB[8], CB[10], or CB[12] compound. Preferably the cucurbituril is a CB[6], CB[7], or CB[8] compound, most preferably a CB[7] compound.

In one embodiment, the other component is another cucurbituril. The other cucurbituril is preferably a compound having a different number of repeat glycoluril units. In other embodiments, the cucurbituril and the other cucurbituril component may be variants and/or derivatives of another. Thus, the present invention also relates to the separation of a cucurbituril from another cucurbituril form.

CB[5] and/or CB[7] may be separated from CB[6] and/or CB[8] on the basis of their solubility in water. CB[5] and CB[7] are soluble in water, CB[6] and CB[8] are not.

The methods described herein relate, in certain embodiments, to the separation of CB[5] from CB[7], and CB[6] from CB[8]. The method of the invention may be used in combination with those methods for the separation of CB[5] and/or CB[7] from CB[6] and/or CB[8].

In one embodiment, the cucurbituril is a CB[7] compound, and the other component is a CB[5] compound.

The separation of CB[7] from CB[5] is particularly difficult as the solubility of these cucurbituril compounds in water is very similar (20-30 mM). Thus, the compounds usually co-crystallise or drop out of solution together as a mixture. The present inventors have therefore found a useful way of separating these particular cucurbituril compounds on the basis of the selective formation of a complex of CB[7] with a guest molecule. The guest molecule does not substantially interact with CB[5].

In one embodiment, the cucurbituril is a CB[6] compound, and the other component is a CB[8] compound.

In one embodiment, the cucurbituril is a CB[8] compound, and the other component is a CB[6] compound.

The present inventors have found a useful way of separating these particular cucurbituril compounds on the basis of the selective formation of a complex of a guest with either CB[6] or CB[8].

Cucurbit[7]uril (CB[7]) is a barrel shaped container molecule which has seven repeat glycoluril units:

References to cucurbituril may also include a reference to a variant or derivative of a cucurbituril.

For example, a variant of a cucurbituril may also include a structure having one, two, three, four or more repeat units that are structurally analogous to glycoluril. The repeat unit may include an ethylurea unit. Where all the units are ethylurea units, the variant is a hemicucurbituril. For example a variant of CB[12] is hemicucurbit[12]uril (shown below).

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

wherein:
n is an integer of at least 5;
X is O, S or $NR^3$, and
—$R^1$ and -$R^2$ are each independently selected from -H and the following optionally substituted groups: —$R^3$, —OH, —OR$^3$, —COOH, —COOR$^3$, —NH$_2$, —NHR$^3$ and —N(R$^3$)$_2$ where —R$^3$ is independently selected from C$_{1-20}$alkyl, C$_{6-20}$carboaryl, and C$_{5-20}$heteroaryl, or where —R$^1$ and/or —R$^2$ is —N(R$^3$)$_2$, both —R$^3$ together form a C$_{5-7}$ heterocyclic ring; or together —R$^1$ and —R$^2$ are C$_{4-6}$alkylene forming a C$_{6-8}$carbocyclic ring together with the uracil frame. It is preferred that —R$^1$ and —R$^2$ are not both —H.

Preferably, n is 5, 6, 7, 8, 10 or 12.

Preferably, X is O.

Preferably —R$^3$ is C$_{1-20}$alkyl, most preferably C$_{1-6}$alkyl. The C$_{1-20}$alkyl group may be linear and/or saturated. Each group —R$^3$ may be independently unsubstituted or substituted. Preferred substituents are selected from: —R$^4$, —OH, —OR$^4$, —SH, —SR$^4$, —COOH, —COOR$^4$, —NH$_2$, —NHR$^4$ and —N(R$^4$)$_2$, wherein —R$^4$ is selected from C$_{1-20}$alkyl, C$_{6-20}$carboaryl, and C$_{5-20}$heteroaryl. The substituents may be independently selected from —COOH and —COOR$_4$.

In some embodiments, —R$^4$ is not the same as —R$^3$. In some embodiments, —R$^4$ is preferably unsubstituted.

Where —R$^1$ and/or —R$^2$ is —OR$^3$, —NHR$^3$ or —N(R$^3$)$_2$, then —R$^3$ is preferably C$_{1-6}$alkyl. In some embodiments, —R$^3$ is substituted with a substituent —OR$^4$, —NHR$^4$ or —N(R$^4$)$_2$. Each —R$^4$ is C$_{1-6}$alkyl and is itself preferably substituted.

Cucurbituril Guest

As noted above, the guest is a compound that is capable of forming a guest-host complex with a cucurbituril. The resulting complex has different physical and/or chemical properties to the cucurbituril.

In a broadest aspect, therefore, the guest is any compound capable of providing a complex having different physical and/or chemical properties to the cucurbituril.

The guest is a compound, which includes a salt, that is capable of forming a complex with the cucurbituril. Where the other component is another cucurbituril, the guest selectively forms a complex with the cucurbituril rather than the other cucurbituril.

In principal, any compound having a suitable binding affinity and selectively may be used in the methods of the present invention. However, the most preferred compounds are ionic liquids as discussed in detail below.

In selecting a compound suitable for use as a guest, consideration may be given to the selectivity of that guest for one cucurbituril over another cucurbituril form. The compound used may be selected based on the size of the moieties that are thought to interact with the cavity of the cucurbituril. The size of these moieties may be sufficiently large to permit complexation only with larger cucurbituril forms.

The guest and the cucurbituril typically form a 1:1 complex. Preferably the guest is a compound (which includes salts) capable of forming a complex which has a binding affinity ($K_a$) of at least $10^3$ M$^{-1}$, of at least $10^4$ M$^{-1}$, of at least $10^5$ M$^{-1}$, of at least $10^6$ M$^{-1}$, of at least $10^7$ M$^{-1}$, of at least $10^8$ M$^{-1}$, of at least $10^9$ M$^{-1}$, of at least $10^{10}$ M$^{-1}$, of at least $10^{11}$ M$^{-1}$, or of at least $10^{12}$ M$^{-1}$.

In one embodiment, the guest is a compound (which includes salts) capable of forming a complex which has a binding affinity in the range $10^4$ to $10^7$ M$^{-1}$.

The term selective may be used to refer to the amount of guest-host complex formed, where the cucurbituril (the first cucurbituril) and a second cucurbituril are present in the mixture. The guest-host complex formed between the first cucurbituril and the guest the may be at least 60 mol %, at least 70 mol %, at least 80 mol %, at least 90 mol %, at least 95 mol %, at least 97 mol %, at least 98 mol %, or at least 99 mol %, of the total amount of guest-host complex formed (for, example taking into account the amount of guest-host complex formed between the second cucurbituril and the guest, if any).

In one embodiment, the guest-host complex formed from the (first) cucurbituril and the guest has a binding affinity that is at least 100 times greater than the binding affinity of a guest host complex formed from the second cucurbituril and the guest. Preferably, the binding affinity is at least $10^3$, at least $10^4$, at least $10^5$, at least $10^6$, or at least $10^7$ greater.

The guest is preferably an ionic liquid.

The ionic liquid typically comprises a cationic organic nitrogen heterocycle, which may be an aromatic nitrogen heterocycle (a heteroaryl) or a non aromatic nitrogen heterocycle. The ionic liquid also typically comprises a counter-anion to the cationic organic nitrogen heterocycle. The nitrogen heteroaryl group is preferably a nitrogen C$_{5-10}$heteroaryl group, most preferably a nitrogen C$_{5-6}$heteroaryl group, where the subscript refers to the total number of atoms in the ring or rings, including carbon and nitrogen atoms. The non aromatic nitrogen heterocycle is preferably a nitrogen C$_{5-6}$heterocycle, where the subscript refers to the total number of atoms in the ring or rings, including carbon and nitrogen atoms. A nitrogen atom in the ring of the nitrogen heterocycle is quaternised.

The counter-anion may be a halide, preferably a bromide. Other counter-anions suitable for use are those that result in a complex that is soluble in water.

The guest is preferably a compound, including a salt, comprising one of the following groups selected from the list consisting of: imidazolium moiety; pyridinium moiety; quinolinium moiety; pyrimidinium moiety; pyrrolium moiety; and quaternary pyrrolidine moiety.

Preferably, the guest comprises an imidazolium moiety. An especially preferred guest is 1-alkyl-3-alkylimidazolium, where the alkyl groups are optionally substituted.

1-Alkyl-3-alkylimidazolium compounds, where the alkyl groups are unsubstituted, are especially suitable for use in the separation of CB[7] from CB[5]. Here, the alkylimidazolium compound forms a complex with CB[7]. The complex is preferably water soluble. The complex may be converted to an insoluble form (for example, by ion exchange) to allow separation from CB[5], which is soluble in water.

1-Alkyl-3-alkylimidazolium compounds, where the alkyl groups are unsubstituted, are especially suitable for use in the separation of CB[6] from CB[8]. Here, the alkylimidazolium compound forms a complex with CB[6]. The complex is preferably water soluble, thereby to allow separation from CB[8], which is insoluble in water.

1-Alkyl-3-alkylimidazolium compounds, where an alkyl group is substituted with aryl (preferably napthyl), are especially suitable for use in the separation of CB[8] from CB[6]. Here, the alkylimidazolium compound forms a complex with CB[8]. The complex is preferably water soluble, thereby to allow separation from CB[6], which is insoluble in water.

The 1-alkyl and 3-alkyl substituents may the same or different. Preferably, they are different.

In one embodiment, the 3-alkyl substituent is methyl, and is preferably unsubstituted. In one embodiment, the 1-alkyl substituent is ethyl or butyl, and each is preferably unsubstituted.

A preferred optional substituent is aryl, preferably C$_{5-10}$aryl. Aryl includes carboaryl and heteroaryl. Aryl groups include phenyl, napthyl and quinolinyl.

In one embodiment, the alkyl groups described herein are linear alkyl groups.

Each alkyl group is independently a $C_{1-6}$alkyl group, preferably a $C_{1-4}$alkyl group.

The aryl substituent may itself be another 1-alkyl-3-substituted-imidazolium moiety (where the alkyl group is attached to the 3-position of the ring).

1-Alkyl-3-methylimidazolium salt ([$C_n$mim]X) ionic liquids have become popular in variety of chemical research areas as "green" solvents.[10] Additionally, [$C_n$mim]X species have received recent attention and have been studied by several groups as good guests for both CB[6] and CB[7] and in some cases are significantly able to increase the solubility of the CB host in neutral water.[11, 12, 13, 14]

CB[7]-[$C_n$mim]X complexes have a wide range of binding affinities ($K_a$) ranging from $10^4$ to $10^7$ $M^{-1}$ and whose water solubility is dependent upon both the alkyl chain length and the counter ion.[13] As both the alkyl chain length and counter ion can easily be altered from a synthetic point of view, they provide a handle for control and an opportunity for use in the purification process.

In another embodiment, the compound preferably comprises a pyridinium moiety.

The guest-host complexes described herein are not limited to those complexes having a ratio of guest to cucurbituril of 1:1. Complexes comprising two guest compounds within a cucurbituril host are also encompassed by the present methods.

Whether or not a complex formed comprises one or two guests depends on the nature of the cucurbituril and the nature the guest. For such complexes it is not essential that each of the guests in the complex be the same, but it may be preferred that they are.

Where the complex comprises two guests within the cucurbituril cavity, the association constant, $K_a$, for that complex is at least $10^6$ $M^{-2}$, of at least $10^7$ $M^{-2}$, of at least $10^8$ $M^{-2}$, of at least $10^9$ $M^{-2}$, of at least $10^{10}$ $M^{-2}$, of at least $10^{11}$ $M^{-2}$, or of at least $10^{12}$ $M^{-2}$.

For CB[6] compounds it has been suggested that short chain 1-alkyl-3-methylimidazolium compounds form 2:1 complexes, whilst longer chain 1-alkyl-3-methylimidazolium compounds form 1:1 complexes.

Where a complex is formed having two guest molecules within a cucurbituril host, it is preferred that the guest molecules are the same. However, the present invention also encompasses methods where the guest molecules are different. Complexes having different guests may be used to finely tune the solubility characteristics of the overall complex. The guest molecules may be chosen on the basis of a preferred formation of a complex with one cucurbituril host over another cucurbituril compound. Where two different guest molecules are used, such molecules are preferably selected from the guest molecules described herein.

For example, the guest molecules may be a charge transfer pair comprising electron rich and electron-deficient compounds. Examples of ternary guest-host complexes formed from different guests are described in the applicant's earlier filing, WO 2009/071899. An example complex is that of a CB[8] molecule hosting a compound comprising a 2,6-dihydroxynapthalene moiety and a compound comprising a N,N'-dimethyldipyridyliumylethylene diiodide.

In one embodiment, where the complex formed comprises two guests, each guest is an ionic liquid. These ionic liquids may be the same or different. Each ionic liquid may be selected from the ionic liquids described herein.

The present invention also encompasses methods whereby a single guest molecule interacts with two identical cucurbituril compounds, thereby to form a guest-host complex comprising two hosts. Such complexes may form where, for example, the guest comprises two moieties that are capable of each independently interacting with a cucurbituril compound.

Where the guest is an ionic liquid, the counter-anion may be used to alter the solubility of the overall complex in a solvent, and preferably in water. Thus, in certain embodiments a halide counter-anion, preferably a bromide counter-anion, may be used to generate a complex that is water soluble. In other embodiments, a $PF_6^-$ counter-anion may be used to generate a complex that is water insoluble. In a preferred method described herein, a water soluble complex having a halide counter ion is generated, and the halide counter-anion is exchanged for a $PF_6^-$ counter-anion, thereby to generate a water insoluble complex that is separable from the other component of the mixture, for example by filtration. In this way both the complex and the other component may be separately collected.

The guest may be used to solubilise a cucurbituril that is insoluble in a solvent, for example water. The guest may be used to form a complex with the cucurbituril that is soluble in that solvent. A mixture comprising a cucurbituril that is insoluble in water and another component that is insoluble in water may be purified by selectively forming a water soluble complex of the cucurbituril and a guest. The water soluble complex may be separated from the water insoluble other component, for example by filtration. In this way both the complex and the other component may be separately collected.

In both cases above, the recovered complex may be decomplexed to obtain the cucurbituril and the guest, which may be suitable for use in a further purification step.

Cucurbituril may find use in cosmetic products or domestic cleaning products and the like. Therefore it is preferred that the guest compounds used in the present methods are not toxic.

Preferred Guest Compounds

Preferred guests for use in the present invention are of the form $H^+X^-$, where $H^+$ is one of the following cations,

| Cation | Structure |
| --- | --- |
| A |  |
| B |  |
| C |  |
| D |  |
| E |  |

| Cation | Structure |
|---|---|
| F |  | and X⁻ is a suitable counter-anion, as defined above. A preferred counter anion is a halide anion, preferably Br⁻.

In a preferred embodiment, cation A or cation B may be used to form a complex with CB[7] or CB[6].

In a preferred embodiment, cation D or cation E may be used to form a complex with CB[8].

Cations A and B may be referred to as 1-ethyl-3-methylimidazolium and 1-butyl-3-methylimidazolium respectively.

Cations D and E may be referred to as 1-naphthalenylm-ethyl-3-methylimidazolium, where D is 1-naphthalen-2-ylm-ethyl-3-methylimidazolium and E is 1-naphthalen-1-ylm-ethyl-3-methylimidazolium.

Additional Guest Compounds

Alternatively or additionally, the guest compounds may be an imidazolium salt of formula (I):

wherein X⁻ is a counter anion;

$R^1$ is independently selected from H and saturated $C_{1-6}$ alkyl;

$R^2$ is independently $C_{1-10}$ alkyl which may optionally contain one or more double or triple bonds, and may be optionally interrupted by a heteroatom selected from —O—, —S—, —NH—, and —B—, and may be optionally substituted.

In one embodiment, X⁻ is independently selected from the group consisting of Cl⁻, Br⁻, I⁻, $BF_4^-$, $PF_6^-$, OH⁻, SH⁻, $HSO_4^-$, $HCO_3^-$, $NTf_2$, $C_2N_5O_4$, $AlCl_4^-$, $Fe_3Cl_{12}^-$, $NO_3^-$, $NMeS_2^-$, $MeSO_3^-$, $SbF_6^-$, $PrCB_{11}H_{11}^-$, $AuCl_4^-$, $HF_2^-$, $NO_2^-$, $Ag(CN)_2^-$, and $NiCl_4^-$. In one embodiment, X⁻ is selected from Cl⁻, Br⁻, and I⁻.

In one embodiment, $R^1$ is selected from H and linear saturated $C_{1-6}$ alkyl.

In one embodiment, $R^2$ is linear $C_{1-10}$ alkyl, which may optionally contain one or more double bonds, and may be optionally interrupted by a heteroatom selected from —O—, —S—, —NH—, and —B—, and may be optionally substituted.

In one embodiment, $R^2$ is linear $C_{1-10}$ alkyl, which may optionally contain one or more double bonds, and may be optionally substituted.

In one embodiment, where a double or triple bond is present, it may be conjugated to the imidazolium moiety. Alternatively, the double or triple bond may not be conjugated to the imidazolium moiety.

In one embodiment, the optional substituents are independently selected from the group consisting of halo, optionally substituted $C_{5-20}$ aryl, —OR³, —OCOR³, =O, —SR³, =S, —BR³, —NR³R⁴, —NR³COR³, —N(R³)CONR³R⁴, —COOR³, —C(O)R³, —C(=O)SR³, —CONR³R⁴, —C(S)R³, —C(=S)SR³, and —C(=S)NR³R⁴, where each of R³ and R⁴ is independently selected from H and optionally substituted saturated $C_{1-6}$ alkyl, $C_{5-20}$ aryl and $C_{1-6}$ alkylene-$C_{5-20}$ aryl.

or R³ and R⁴ may together may form an optionally saturated 5-, 6- or 7-membered heterocyclic ring which is optionally substituted with a group —R³.

In one embodiment, the optional substituents are independently selected from the group consisting of halo, optionally substituted $C_{5-20}$ aryl, —OR³, —OCOR³, —NR³R⁴, —NR³COR³, —N(R³)CONR³R⁴, —COOR³, —C(O)R³, and —CONR³R⁴, where R³ and R⁴ are defined as above.

Each $C_{5-20}$ aryl group may be independently selected from a $C_{6-20}$ carboaryl group or a $C_{5-20}$ heteroaryl group.

Examples of $C_{6-20}$ carboaryl groups include phenyl and napthyl.

Examples of $C_{5-20}$ heteroaryl groups include pyrrole (azole) ($C_5$), pyridine (azine) ($C_6$), furan (oxole) ($C_5$), thiophene (thiole) ($C_5$), oxazole ($C_5$), thiazole ($C_5$), imidazole (1,3-diazole) ($C_5$), pyrazole (1,2-diazole) ($C_5$), pyridazine (1,2-diazine) ($C_6$), and pyrimidine (1,3-diazine) ($C_6$) (e.g., cytosine, thymine, uracil).

Each $C_{5-20}$ aryl is preferably selected from optionally substituted phenyl, napthyl and imidazolium.

Each $C_{5-20}$ aryl group is optionally substituted. The optional substituents are independently selected from halo, $C_{1-6}$ alkyl, —OR³, —OCOR³, —NR³R⁴, —NR³COR³, —N(R³)CONR³R⁴, —COOR³, —C(O)R³, and —CONR³R⁴, where R³ and R⁴ are defined as above.

In one embodiment, each $C_{5-20}$ aryl group is optionally substituted with $C_{1-6}$ alkyl.

Where the $C_{5-20}$ aryl group is an imidazolium, such is preferably substituted at nitrogen with a group $R^1$ (thereby forming a quaternary nitrogen).

The compound of formula (I) comprises an imidazolium moiety having a substituent $R^2$ at the 1-position and a substituent $R^1$ at the 3-position. In a further aspect of the invention, the compound of formula (I) may be optionally further substituted at the 2-, 4- or 5-positon with a group $R^4$, wherein $R^4$ has the same meaning as $R^1$.

The embodiments above are combinable in any combination, as appropriate.

Complex

In a preferred embodiment, the complex formed from the guest and the cucurbituril is soluble in water.

The complex may be made insoluble in water to aid separation from the other component in the mixture. For example, where the guest compound is a salt, such as an ionic liquid, the complex formed is also a salt. The counter ion of the guest compound in the complex may be exchanged for another counter ion. That counter ion may cause a change in the solubility of the overall complex. Preferably, the ion exchange causes a change in the water solubility of the complex. In one embodiment, the ion exchange results in a complex having lower water solubility. The complex may be converted to a substantially insoluble form. In another embodiment, the ion exchange results in a complex having higher water solubility.

The timescale for complex formation may be at least 6 hours, at least 12 hours, at least 24 hours, at least 48 hours, or at least 72 hours.

The decomplexation of the complex to separate guest and cucurbituril components is described in more detail in the Separation section below.

The formation of the complex may be monitored using those techniques familiar to one skilled in the art. For example, NMR (including $^1$H and 2D NMR techniques), UV/vis, fluorescence, IR, calometric titration and specific viscosity measurements may be used to monitor the formation of a guest-host complex in the mixture, and may be used to indentify the complex after isolation. Such techniques may also be used to determine the purity of the complex after separation.

Separation

The guest-host complex is purified from the other component of the mixture. This may be referred to as the separation of the cucurbituril, or the complex, from the other component.

The methods described herein relate to the purification of a cucurbituril from a mixture. The cucurbituril may be purified as a guest-host complex, or may be obtained as the cucurbituril after decomplexation.

The methods of purification refer to the separation of the cucurbituril from at least one other component of the mixture. The separated cucurbituril, which may be in a complex, is substantially free of the other component.

In one embodiment, the separated cucurbituril is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

In one embodiment, the other component represents no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

The method comprises a separation step whereby the guest-host complex is separated from the other component of the mixture. The separation of the complex from the other component may be achieved using those purification techniques familiar to those of skill in the art. The separation may optionally involve the additional separation of the complex from the mixture solvent.

In one embodiment, the complex formed from the guest and the cucurbituril is soluble in water. In the purification step, the complex may be made insoluble for separation from the other component, which is soluble in water.

In a preferred embodiment, the purification comprises the step separating a complex from the other component by one or more of filtration, chromatography, separation, and crystallisation.

The purification step may also comprise one or more ion exchange step. The ion exchange may be before or after any filtration, chromatography, separation, or crystallisation step.

As is apparent from the detailed description of the invention above, the method described herein may also be used to purify the other component from the mixture.

The present method is of particular advantage in purifying mixtures where the cucurbituril and the other component (which may be another cucurbituril) have similar physical and/or chemical properties thereby preventing or complicating the isolation of one from the other. The formation of a complex of the cucurbituril with a guest alters the physical and/or chemical properties of the cucurbituril, which allow the cucurbituril (in a complex) to be separated from the other component. It is apparent that this allows the other component to be purified from the cucurbituril. Thus, the methods as described herein as relating to methods for the purification of a cucurbituril from a mixture (the mixture further comprising another component), may also be read as referring to methods for the purification of a component from a mixture (the mixture further comprising a cucurbituril).

In a preferred embodiment, the complex is decomplexed by way of a solid state metathesis (SSM) reaction. The SSM reaction may be performed in a solvent in which the complex is insoluble. The SSM reaction may be performed in a solvent in which the at least on of the guest or the cucurbituril soluble.

Other decomplexation methods may be used, such as soxhlate extraction and reflux with various solvents, such as MeOH, DCM, and diethyl ether. However, these techniques may not be suitable for all cucurbituril complexes, including for example the preferred CB[7]-[$C_n$mim] complexes described herein.

The timescale for decomplexation may be at least 6 hours, at least 12 hours, at least 24 hours, at least 48 hours (2 days), at least 72 hours (3 days), or at least 168 hours (1 week).

The purification methods described herein permit recycling of the guest for use in further cycles of purification. In the decomplexation step, the guest may be isolated and retained for further use. In this way, the present method is particularly advantageous as it requires only a limited amount of guest material.

In a preferred embodiment, if required, the isolated guest is converted to a form suitable for use in a further purification step.

In the preferred embodiments described herein, the guest may be obtained in a salt form that, if used in a purification method of the invention, would not yield a soluble complex. The salt from may therefore be converted to a form that would yield a soluble complex, when used. For example, the counter-anion may be exchanged for a counter-anion that would yield a soluble complex. In a preferred embodiment, an isolated guest having a $PF_6^-$ counter-anion is converted to a guest having a Br counter-anion.

Preferred Method

In a preferred embodiment there is provided a method of purifying CB[7] from a mixture, the method comprising the steps of:
  providing a mixture comprising CB[7] and CB[5];
  introducing to the mixture a CB[7] guest, thereby to form a guest-host complex between the guest and the CB[7], wherein the CB[7] guest is an ionic liquid;
  separating the guest-host complex from CB[5] thereby to purify the CB[7] from the mixture.

The ionic liquid may be a 1-alkyl-3-alkylimidazolium salt. The salt is preferably a bromide salt.

The complex is preferably soluble in water. The separation may comprise the step of converting the water soluble complex to a water insoluble complex. This step may include ion exchange. Where the 1-alkyl-3-alkylimidazolium salt is a bromide salt, the corresponding complex may be made insoluble by replacement of the bromide anion with a $PF_6^-$ anion. The insoluble complex may be separated from the soluble CB[5], for example by filtration. CB[5] may be recovered from the aqueous solution. It may be further purified, for example by recrystalisation.

The complex may be decomplexed to yield CB[7] and the guest. In a preferred embodiment, the complex is decomplexed by way of a solid state metathesis reaction.

The complex may be first resolubilised in water, for example by ionic exchange, then precipitated in a polar organic solvent. The precipitated complex may then be allowed to undergo a solid sate metathesis reaction to yield CB[7] and guest.

In another preferred embodiment there is provided a method of purifying CB[6] from a mixture further comprising CB[8], the method comprising the steps of:

providing a mixture comprising CB[6] and CB[8];
introducing to the mixture a guest for CB[6] or CB[8], thereby to form a guest-host complex between the guest and the CB[6] or CB[8], wherein the CB[6] or CB[8] guest is an ionic liquid;
separating the guest-host complex thereby to purify the CB[6] or CB[8] from the mixture.

The preferred methods relate to the use of an ionic liquid, although in principle any compound that is capable of forming a complex selectively with one cucurbituril form over another may be suitable for use in these methods.

The mixtures described above include a solvent as well as the cucurbituril compounds described. The solvent is preferably water.

In each of the methods above, a reference to the formation of a guest-host complex is also a reference to complex comprising two guest molecules that may be the same of different. Where appropriate, a reference to a guest may be construed as a reference to two different guest molecules.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental

Figure 1:
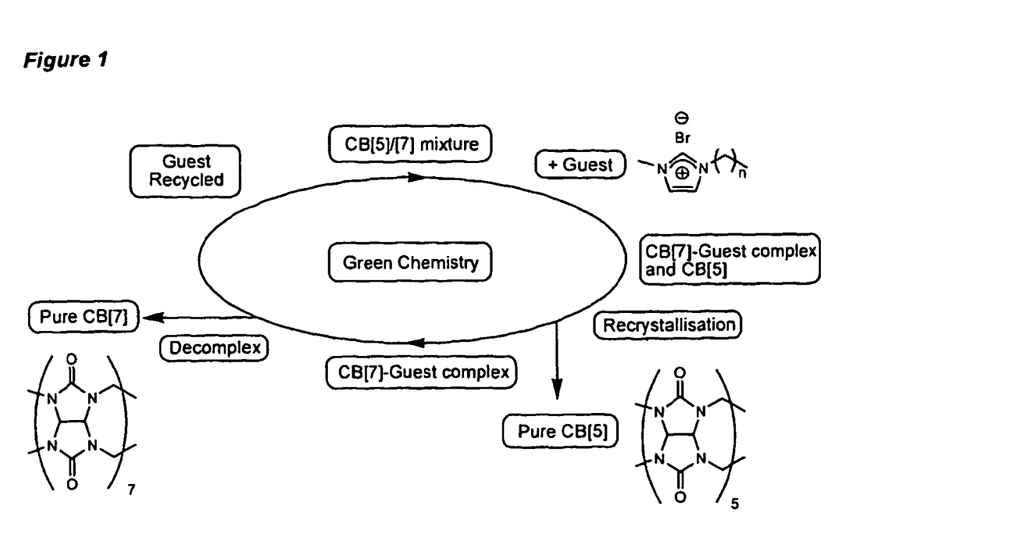
FIG. 1 is a schematic representation of a method for the purification a cucurbituril from a mixture according to an embodiment of the invention. The mixture comprises CB[7] and CB[5], and the CB[7] guest is a 1-alkyl-3-methylimidazolium.

The separation of a mixture of CB[5] and CB[7] is described below, with particular reference to FIGS. 1 and 2. For reference, [$C_n$mim] refers to 1-alkyl-3-methylimidazolium, where n is the number of carbon atoms in the 1-alkyl group.

Figure 2:
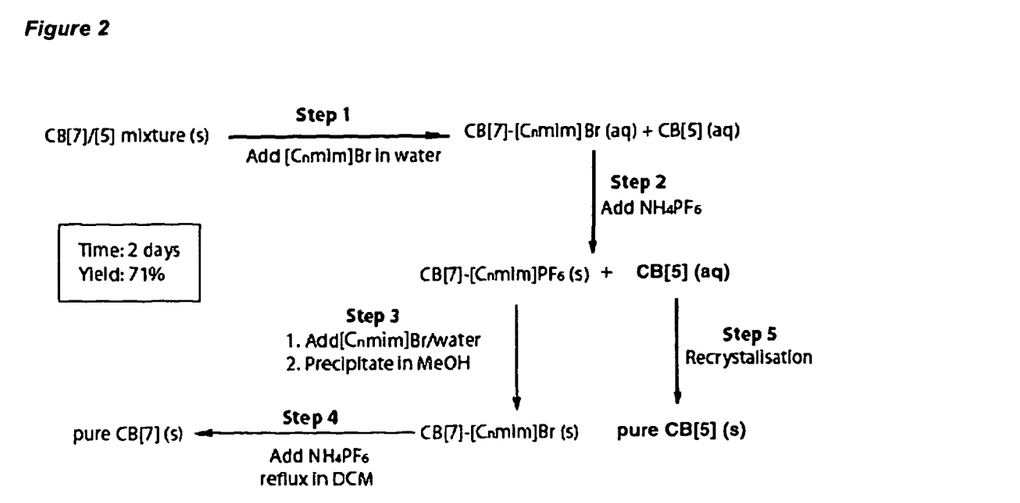
FIG. 2 shows the stepwise procedure for the purification a cucurbituril from a mixture according to an embodiment of the invention. At each step, the components were fully isolated. The starting material (2 g) contains CB[7] (80%) and CB[5] (12%), and produces pure CB[7] 1.41 g. The left solution is collected and further purified CB[5] by step (5) (yield of step (5) is 46%). [$C_n$mim]X is extracted from waste solvent produced by step (3) (4) (5).

The starting material (2 g) contained CB[7] (80%) and CB[5] (12%). [$C_n$mim]Br can be employed to increase the solubility of CB[7] in water as shown in step 1 of FIG. 2. The CB[7]-[$C_n$mim] complex formed can be isolated from CB[5] by adding $NH_4PF_6$ salt into the system resulting in a CB[7]-[$C_n$mim]$PF_6$ complex which has poor solubility and precipitates from water. The CB[5] remains in solution: its cavity is too small to bind the [$C_n$mim] guest, and addition of the $PF_6$ salt does not reduce CB[5]'s solubility.

In fact, addition of $NH_4PF_6$ to the system is believed to produce $NH_4Br$ which forms CB[5]-$NH_4^+$ complexes through portal binding. This may actually enhance the solubility of CB[5] in water. Pure CB[5] can be isolated by recrystallisation from the filtered solution.

Once CB[5] has been removed from the mixture, a final key step in the purification method for CB[7] is the dissociation of the CB[7]-[$C_n$mim] complex. As CB[7] has a reasonable solubility in water, and [$C_n$mim]PF6 is soluble in a wide variety of common organic solvents, it was reasoned that decomplexation might be afforded by either precipitation or successive extraction. Attempts to decomplex the system by exhaustive soxhlate extraction and reflux with various solvents, such as MeOH, DCM, and diethyl ether all failed and none of these techniques liberated the ionic liquid guest from the CB[7] cavity.

As a solution-based method proved difficult to achieve, a dissociation based on a solid-state ion exchange was therefore attempted.

After successful removal of CB[5], CB[7]-[$C_n$mim]$PF_6$ is converted back to the bromide counter ion in step 3 (FIG. 2), followed by dissociation of the CB[7]-[$C_n$mim]Br complex through a solid state metathesis (SSM) reaction.[15, 16, 17] The reaction used $NH_4PF_6$ in refluxing DCM. The SSM reaction was shown to be useful in this particular case as both starting materials were not soluble in DCM. However, as the reaction proceeded, [$C_n$mim]$PF_6$ formed and immediately partitioned into DCM leaving $NH_4Br$ and CB[7] in the solid state. The selective removal of [$C_n$mim]$PF_6$ from the reaction state provided the required driving force for quantitative decomplexation. The reaction was followed by $^1$H NMR and was stopped when all the complex was observed to have dissociated. The resulting CB[7] solid was then filtered and washed with MeOH. The free [$C_n$mim]$PF_6$ may be extracted from the DCM solution for later re-use.

Figure 3:
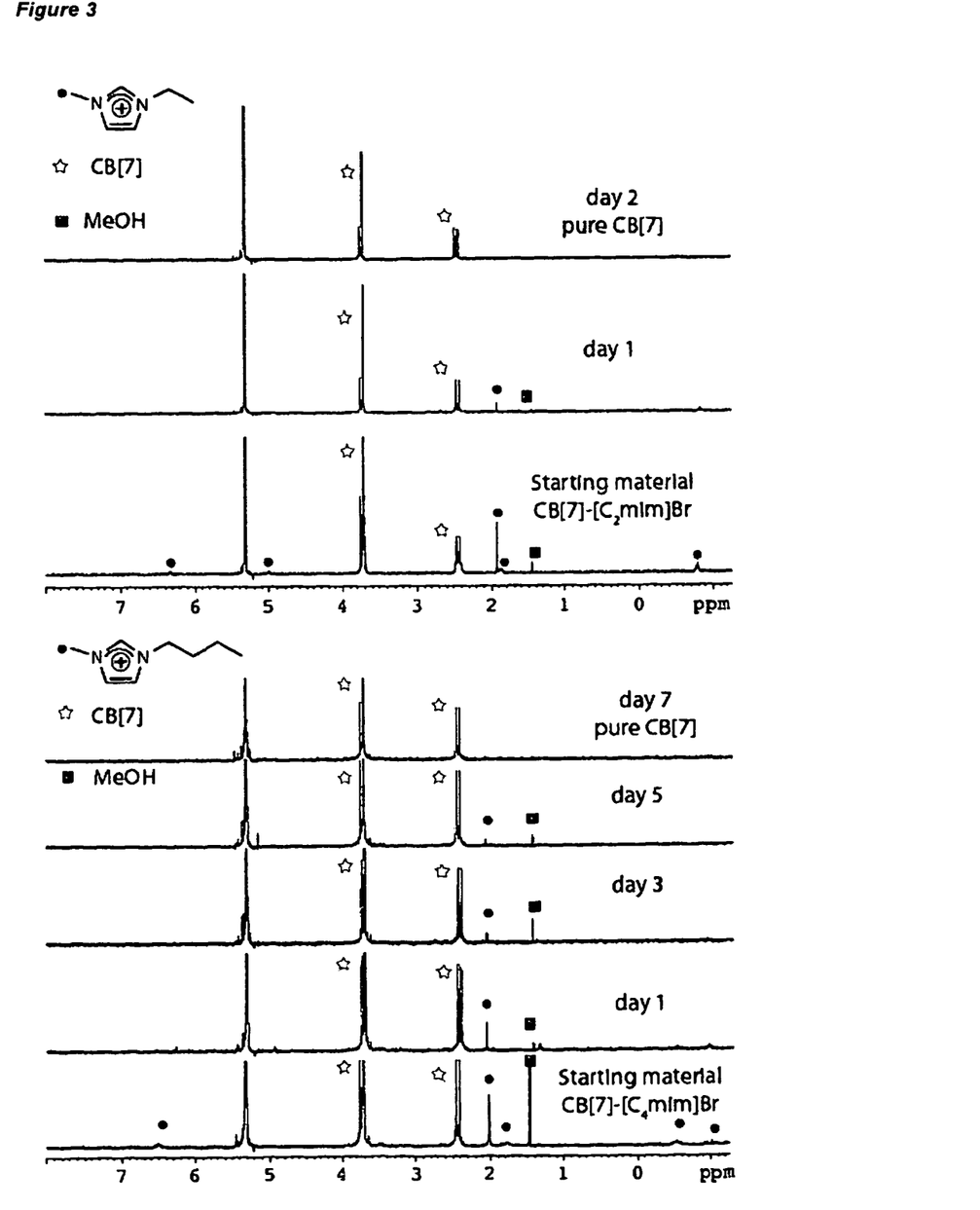
FIG. 3 shows the 1H NMR spectrum (in 20% DCl, CB[7]'s peaks (star) are at 3.7 and 2.4 ppm) of the dissociation of CB[7]-[$C_2$mim]Br complex (top) and of CB[7]-[$C_4$mim]Br complex (bottom) over time. The dots (peak at 1.9 ppm) represent the protons of the methyl group on imidazolium and others are binding peaks of imidazolium in CB[7]. The squares represent the protons of the methyl group of MeOH.

The timescale of dissociation of the CB[7]-[$C_8$mim]Br complex through the SSM reaction depends highly on the binding constant of the complex. As shown in FIG. 3, the imidazolium (which is indicated by the peak of the methyl group at 2 ppm) has been removed from the complex in both systems (top spectra in both stack plots). The binding constant of CB[7]-[$C_4$mim]Br ($K_a>10^7$ M$^{-1}$) is much greater than that of CB[7]-[$C_2$mim]Br ($K_a>10^5$ M$^{-1}$),[13] and therefore required a longer dissociation time. With [$C_2$mim]Br the decomplexation procedure required only two days, however, using [$C_4$mim]Br required an entire week under the same reaction conditions.

Solvent choice is an important component in designing this separation route via an SSM reaction. When MeOH was used instead of DCM, no reaction took place as $NH_4PF_6$ is also soluble in MeOH, thereby preventing any ion exchange in the solid state. Whilst DCM does not solubilise any of the starting materials, it solubilises one of the products, which in turn drives the equilibrium to favour the dissociation of the complex:

In summary, both CB[7] and CB[5] can be easily isolated in very good yields: CB[7]>70%, and in excellent purity in comparison with previously published separation-based routes. Moreover, the "waste" material from each step can be recycled, thus, leading to a near quantitative recovery loop.

The imidazolium ionic liquids were isolated from the solution waste through a straight forward extraction process and were recycled for subsequent use.

[C$_n$mim]Br was synthesised from methyl imidazole and the appropriate 1-bromo alkyl. The starting CB[5]/[7] mixture used in these experiments was obtained from a standard CB[n] synthesis.[6, 7] The overall yield of CB[7] and CB[5] is 19.9% and 6.4%, respectively, using the procedure disclosed in this paper, produces both greater isolated yield and higher purity of both CB[7] and CB[5] than in previously published routes for all preparing all CB[n] species in a single reaction.

The waste from each step has also been carefully controlled. The non-recycled salt (NH4Br) was filtered from the solution after the ion exchange process. The waste solvents (DCM and methanol) were collected from the isolation process and 90% of both of these solvents could be recycled for further use in this procedure after distillation. Finally, 80% of the [Cnmim]PF$_6$ was isolated from the solvent and was reused after a simple ion exchange form PF$_6$ back to the original Br counterion.

REFERENCES

All documents mentioned in this specification are incorporated herein by reference in their entirety.

[1] J. Lagona, P. Mukhopadhyay, S. Chakrabarti and L. Isaacs, Angew. Chem. Int. Ed., 2005, 44, 4844-4870.
[2] J. W. Lee, S. Samal, N. Selvapalam, H.-J. Kim and K. Kim, Acc. Chem. Res., 2003, 36, 621-630.
[3] A. Hennig, H. Bakirci and W. Nau, Nat. Methods, 2007, 4, 629-632.
[4] S. Gadde, E. K. Batchelor, J. P. Weiss, Y. Ling and A. E. Kaifer, J. Am. Chem. Soc., 2008, 130, 17114-17119.
[5] Y. Zeng, Y. Li, M. Li, G. Yang and Y. Li, J. Am. Chem. Soc., 2009, 131, 9100-9106.
[6] J. Kim, I.-S. Jung, S.-Y. Kim, E. Lee, J.-K. Kang, S. Sakamoto, K. Yamaguchi and K. Kim, J. Am. Chem. Soc., 2000, 122, 540-541.
[7] A. I. Day, A. P. Arnold, R. J. Blanch and B. Snushall, J. Org. Chem., 2001, 66, 8094-8100.
[8] C. Marquez, F. Huang and W. Nau, IEEE T. NANOBIOSCI., 2004, 3, 39-45.
[9] W.-H. Huang, P. Y. Zavalij and L. Isaacs, J. Am. Chem. Soc., 2008, 130, 8446-8454.
[10] S. Dzyuba and R. Bartsch, ChemPhysChem., 2008, 3, 161.
[11] L. Liu, N. Zhao and O. A. Scherman, Chem. Commun., 2008, 3, 1070.
[12] P. Montes-Navajas, A. Corma and H. Garcia, J. Mol. Catal. A-Chem., 2008, 279, 165-169.
[13] Z. Miskolczy, L. Bicz'ok, M. Megyesi, and I. Jablonkai, J. Phys. Chem. B, 2009, 113, 1645-1651.
[14] V. Kolman, R. Marek, Z. Strelcova, P. Kulhanek, M. Necas, J. Svec and V. Sindelar, Chem. Eur. J., 2009, 15, 6296-6931.
[15] P. R. Bonneau, R. F. Jarvis and R. B. Kaner, Nature, 1991, 349, 510-512.
[16] K. Gibson, M. Strbele, B. Blaschkowski, J. Glaser, M. Weisser, R. Srinivasan, H.-J. Kolb and Hans-Jrgen Meyer, Z. Anorg. Allg. Chem., 2003, 629, 1863-1870.
[17] Y.-S. He, Z.-F. Ma, X.-Z. Liao and Y. Jiang, J. Power Sources, 2007, 163, 1053-1058.
[18] D. Jiao, F. Biedermann, F. Tian and O. A. Scherman, J. Am. Chem. Soc., 2010, 132, 15734-15743. Published on Web 14 Oct. 2010.
[19] WO 2009/071899.

The invention claimed is:

1. A method for the purifying a cucurbituril from a mixture, the method comprising the steps of:
   providing a mixture comprising the cucurbituril and at least one other component in a solvent;
   introducing to the mixture a cucurbituril guest or guests, thereby to form a guest-host complex between the guest or guests and the cucurbituril;
   separating the guest-host complex from at least one component of the mixture thereby to purify the cucurbituril from the other component,
   wherein the cucurbituril guest or guests comprises a cationic organic nitrogen heterocycle, and the other component is another cucurbituril.

2. The method of claim 1, wherein the cucurbituril is cucurbit[7]uril.

3. The method of claim 1, wherein the other component is cucurbit[5]uril.

4. The method of claim 1, wherein the cucurbituril is cucurbit[6]uril or cucurbit[8]uril.

5. The method of claim 4, wherein
   the other component is cucurbit[8]uril, where the cucurbituril is cucurbit[6]uril, or
   the other component is cucurbit[6]uril, where the cucurbituril is cucurbit[8]uril.

6. The method of claim 1, wherein the separating step includes a step of ion exchange.

7. The method of claim 6, wherein the cationic organic nitrogen heterocycle comprises a group selected from the list consisting of:
   imidazolium moiety;
   pyridinium moiety;
   quinolinium moiety;
   pyrimidinium moiety;
   pyrrolium moiety; and
   quaternary pyrrolidine moiety.

8. The method of claim 7, wherein the cationic organic nitrogen heterocycle comprises an imidazolium moiety.

9. The method of claim 8, wherein the cucurbituril guest or guests is a 1-alkyl-3-alkylimidazolium salt, wherein each alkyl group is independently optionally substituted.

10. The method of claim 8, wherein the cucurbituril guest or guests is a 1-alkyl-3-methylimidazolium salt, wherein the 1-alkyl group is independently optionally substituted.

11. The method of claim 8, wherein the cacurbituril guest or guests is a 1-ethyl-3-methylimidazolium salt, a 1-butyl-3-methylimidazolium salt, or a 1-naphthalenylmethyl-3-methylimidazolium salt.

12. The method of claim 1 wherein the mixture is an aqueous mixture.

13. The method of claim 1 further comprising the step of decomplexing the separated guest-host complex, and purifying the cucurbituril from the cucurbituril guest or guests.

* * * * *